(12) United States Patent
Cutrer et al.

(10) Patent No.: US 7,862,497 B2
(45) Date of Patent: Jan. 4, 2011

(54) BRACHYTHERAPY DEVICE HAVING SEED TUBES WITH INDIVIDUALLY-SETTABLE TISSUE SPACINGS

(75) Inventors: L. Michael Cutrer, Huntington Beach, CA (US); Fredrick Wintch, Snohomish, WA (US); Richard A. Terwilliger, Venice, CA (US); John Zhang, Lake Forest Park, WA (US); David Bossi, Simi Valley, CA (US)

(73) Assignee: Portola Medical, Inc., Portola Valley, CA (US)

( * ) Notice: Subject to any disclaimer, the term of this patent is extended or adjusted under 35 U.S.C. 154(b) by 474 days.

(21) Appl. No.: 11/935,348

(22) Filed: Nov. 5, 2007

(65) Prior Publication Data

US 2008/0146862 A1 Jun. 19, 2008

Related U.S. Application Data

(63) Continuation of application No. 11/379,739, filed on Apr. 21, 2006, now abandoned.

(60) Provisional application No. 60/864,288, filed on Nov. 3, 2006.

(51) Int. Cl.
*A61N 5/00* (2006.01)
(52) U.S. Cl. .......................................................... 600/3
(58) Field of Classification Search .................. 600/1–8; 606/191–195
See application file for complete search history.

(56) References Cited

U.S. PATENT DOCUMENTS

| 3,224,432 A | 12/1965 | Billingsley |
| 3,807,326 A | 4/1974 | Rocoplan et al. |
| 3,872,856 A | 3/1975 | Clayton |
| 3,927,325 A | 12/1975 | Hungate et al. |
| 4,434,789 A | 3/1984 | Kumar |
| 4,584,991 A | 4/1986 | Tokita et al. |
| 4,763,642 A | 8/1988 | Horowitz |
| 4,815,449 A | 3/1989 | Horowitz |

(Continued)

FOREIGN PATENT DOCUMENTS

BE 898 752 B1 5/1984

(Continued)

OTHER PUBLICATIONS

U.S. Appl. No. 60/625,355, filed Nov. 5, 2004, White et al.

(Continued)

*Primary Examiner*—Samuel G Gilbert
(74) *Attorney, Agent, or Firm*—McDermott Will & Emery LLP

(57) ABSTRACT

A brachytherapy device may include a plurality of rods, each configured to move between a straightened position and a bowed position, the plurality of rods configured to collectively form a shaft while each rod is in the straightened position and to collectively form at least one cage while at least some of the rods are in the bowed position, at least some of the rods having lumens that are configured to receive and hold radioactive material. A brachytherapy device may further include a rotatable mechanism configured to cause at least some of the plurality of rods to move between the straightened position and the bowed position upon rotation of the rotatable mechanism.

7 Claims, 15 Drawing Sheets

U.S. PATENT DOCUMENTS

| | | |
|---|---|---|
| 4,976,680 A | 12/1990 | Hayman et al. |
| 5,007,437 A | 4/1991 | Sterzer |
| 5,050,930 A | 9/1991 | Schuster et al. |
| 5,125,925 A | 6/1992 | Lundahl |
| 5,147,282 A | 9/1992 | Kan |
| 5,317,616 A | 5/1994 | Swerdloff et al. |
| 5,336,178 A | 8/1994 | Kaplan et al. |
| 5,345,936 A | 9/1994 | Pomeranz et al. |
| 5,411,466 A | 5/1995 | Hess |
| 5,429,582 A | 7/1995 | Williams |
| 5,431,648 A | 7/1995 | Lev |
| 5,484,384 A | 1/1996 | Fearnot |
| 5,540,659 A | 7/1996 | Teirstein |
| 5,611,767 A | 3/1997 | Williams |
| 5,623,940 A | 4/1997 | Daikuzono |
| 5,643,171 A | 7/1997 | Bradshaw et al. |
| 5,653,683 A | 8/1997 | D'Andrea |
| 5,662,580 A | 9/1997 | Bradshaw et al. |
| 5,678,572 A | 10/1997 | Shaw et al. |
| 5,683,345 A | 11/1997 | Waksman et al. |
| 5,688,220 A | 11/1997 | Verin et al. |
| 5,720,717 A | 2/1998 | D'Andrea |
| 5,730,698 A | 3/1998 | Fischell et al. |
| 5,817,104 A | 10/1998 | Bilitz et al. |
| 5,836,868 A | 11/1998 | Ressemann et al. |
| 5,840,008 A * | 11/1998 | Klein et al. .................... 600/3 |
| 5,851,171 A | 12/1998 | Gasson |
| 5,855,546 A | 1/1999 | Hastings et al. |
| 5,863,284 A | 1/1999 | Klein |
| 5,863,285 A | 1/1999 | Coletti |
| 5,879,282 A | 3/1999 | Fischell et al. |
| 5,904,680 A | 5/1999 | Kordis et al. |
| 5,910,101 A | 6/1999 | Andrews et al. |
| 5,910,102 A * | 6/1999 | Hastings ....................... 600/3 |
| 5,913,813 A | 6/1999 | Williams et al. |
| 5,916,143 A | 6/1999 | Apple et al. |
| 5,931,774 A | 8/1999 | Williams et al. |
| 5,938,582 A | 8/1999 | Ciamacco, Jr. et al. |
| 5,968,040 A | 10/1999 | Swanson et al. |
| 6,011,995 A | 1/2000 | Guglielmi et al. |
| 6,013,019 A | 1/2000 | Fischell et al. |
| 6,022,308 A | 2/2000 | Williams |
| 6,030,333 A | 2/2000 | Sioshansi et al. |
| 6,036,631 A | 3/2000 | McGrath et al. |
| 6,050,930 A | 4/2000 | Teirstein |
| 6,059,812 A | 5/2000 | Clerc et al. |
| 6,066,083 A | 5/2000 | Slater et al. |
| 6,074,339 A | 6/2000 | Gambale et al. |
| 6,083,148 A | 7/2000 | Williams |
| 6,149,574 A | 11/2000 | Trauthen et al. |
| 6,152,869 A | 11/2000 | Park et al. |
| 6,196,963 B1 | 3/2001 | Williams |
| 6,196,996 B1 | 3/2001 | Teirstein |
| 6,200,257 B1 | 3/2001 | Winkler |
| 6,213,976 B1 | 4/2001 | Trerotola |
| 6,216,043 B1 | 4/2001 | Swanson et al. |
| 6,217,503 B1 | 4/2001 | Weinberger et al. |
| 6,217,585 B1 * | 4/2001 | Houser et al. ............... 606/108 |
| 6,238,374 B1 | 5/2001 | Winkler |
| 6,263,236 B1 | 7/2001 | Kasinkas et al. |
| 6,267,775 B1 | 7/2001 | Clerc et al. |
| 6,338,709 B1 | 1/2002 | Geoffrion et al. |
| 6,391,026 B1 | 5/2002 | Hung et al. |
| 6,409,652 B1 | 6/2002 | Kamdar et al. |
| 6,413,203 B1 | 7/2002 | Sahatjian |
| 6,413,204 B1 | 7/2002 | Winkler et al. |
| 6,482,142 B1 | 11/2002 | Winkler et al. |
| 6,537,194 B1 | 3/2003 | Winkler |
| 6,554,760 B2 | 4/2003 | Lamoureux et al. |
| 6,589,158 B2 | 7/2003 | Winkler |
| 6,607,476 B1 | 8/2003 | Barnhart |
| 6,607,477 B1 | 8/2003 | Longton et al. |
| 6,607,478 B2 | 8/2003 | Williams |
| 6,638,727 B1 | 10/2003 | Hung et al. |
| 6,642,010 B2 | 11/2003 | Love et al. |
| 6,652,548 B2 | 11/2003 | Evans et al. |
| 6,659,105 B2 | 12/2003 | Burbank et al. |
| 6,673,006 B2 | 1/2004 | Winkler |
| 6,676,658 B2 | 1/2004 | Burbank et al. |
| 6,685,718 B1 | 2/2004 | Wyzgala et al. |
| 6,695,760 B1 | 2/2004 | Winkler et al. |
| 6,712,816 B2 | 3/2004 | Hung et al. |
| 6,743,184 B2 | 6/2004 | Sampson et al. |
| 6,749,555 B1 | 6/2004 | Winkler et al. |
| 6,770,058 B1 | 8/2004 | Liprie |
| 6,840,936 B2 | 1/2005 | Sliwa, Jr. et al. |
| 6,855,160 B1 | 2/2005 | Gambale et al. |
| 6,872,183 B2 | 3/2005 | Sampson et al. |
| 6,893,450 B2 | 5/2005 | Foster |
| 6,923,754 B2 | 8/2005 | Lubock |
| 6,955,641 B2 | 10/2005 | Lubock |
| 6,976,949 B2 | 12/2005 | Winkler et al. |
| 6,994,688 B2 | 2/2006 | Brauckman et al. |
| 7,063,670 B2 | 6/2006 | Sampson et al. |
| 2001/0021826 A1 | 9/2001 | Winkler |
| 2002/0133151 A1 | 9/2002 | Hung et al. |
| 2002/0173816 A1 | 11/2002 | Hung |
| 2002/0193653 A1 | 12/2002 | Winkler |
| 2003/0022161 A1 | 1/2003 | Love et al. |
| 2003/0032851 A1 | 2/2003 | Apple et al. |
| 2003/0039959 A1 | 2/2003 | Love et al. |
| 2003/0049262 A1 | 3/2003 | Love et al. |
| 2003/0092957 A1 | 5/2003 | Scott et al. |
| 2003/0149329 A1 | 8/2003 | O'Foghludha |
| 2003/0191412 A1 | 10/2003 | Sampson et al. |
| 2004/0016728 A1 | 1/2004 | Liu et al. |
| 2004/0023912 A1 | 2/2004 | Hung |
| 2004/0029202 A1 | 2/2004 | Love et al. |
| 2004/0054368 A1 | 3/2004 | Truckai et al. |
| 2004/0091423 A1 | 5/2004 | Hung et al. |
| 2004/0109823 A1 | 6/2004 | Kaplan |
| 2004/0116767 A1 | 6/2004 | Lebovic et al. |
| 2004/0167372 A1 | 8/2004 | Winkler et al. |
| 2004/0191854 A1 | 9/2004 | Lapen et al. |
| 2004/0210101 A1 | 10/2004 | Winkler |
| 2004/0215099 A1 | 10/2004 | Sampson et al. |
| 2004/0224347 A1 | 11/2004 | Love et al. |
| 2005/0004471 A1 | 1/2005 | Hogendijk et al. |
| 2005/0027157 A1 | 2/2005 | Winkler et al. |
| 2005/0085681 A1 | 4/2005 | Stubbs et al. |
| 2005/0101823 A1 | 5/2005 | Linares et al. |
| 2005/0101824 A1 | 5/2005 | Stubbs |
| 2005/0101825 A1 | 5/2005 | Winkler et al. |
| 2005/0101860 A1 | 5/2005 | Patrick et al. |
| 2005/0107653 A1 | 5/2005 | Patrick et al. |
| 2005/0113629 A1 | 5/2005 | Patrick et al. |
| 2005/0124843 A1 | 6/2005 | Singh |
| 2005/0131267 A1 | 6/2005 | Talmadge |
| 2005/0131268 A1 | 6/2005 | Talmadge |
| 2005/0131269 A1 | 6/2005 | Talmadge |
| 2005/0137498 A1 | 6/2005 | Sakal et al. |
| 2005/0137499 A1 | 6/2005 | Sheets et al. |
| 2005/0149159 A1 | 7/2005 | Andreas et al. |
| 2005/0182286 A1 | 8/2005 | Lubock |
| 2005/0240073 A1 | 10/2005 | Apffelstaedt et al. |
| 2006/0014997 A1 | 1/2006 | Kindlein et al. |
| 2006/0020156 A1 | 1/2006 | Shukla |
| 2006/0047178 A1 | 3/2006 | Winkler et al. |
| 2006/0063961 A1 | 3/2006 | Drobnik et al. |
| 2006/0094923 A1 | 5/2006 | Mate |
| 2006/0100475 A1 | 5/2006 | White et al. |
| 2006/0116546 A1 | 6/2006 | Eng |
| 2006/0129128 A1 | 6/2006 | Sampson |
| 2006/0135956 A1 | 6/2006 | Sampson et al. |

| | | | |
|---|---|---|---|
| 2007/0049786 | A1 | 3/2007 | Edmundson |
| 2007/0106108 | A1 | 5/2007 | Hermann et al. |
| 2007/0142695 | A1 | 6/2007 | White et al. |

FOREIGN PATENT DOCUMENTS

| | | | |
|---|---|---|---|
| CA | 2296430 | B1 | 6/2004 |
| CA | 2394562 | B1 | 11/2004 |
| DE | 195 13 831 | C1 | 2/1996 |
| DE | 195 47 579 | C1 | 3/1997 |
| EP | 810004 | A2 | 12/1997 |
| EP | 8676200 | | 9/1998 |
| EP | 0 998 330 | A1 | 5/2000 |
| EP | 0 770 258 | B1 | 10/2001 |
| EP | 955 071 | B1 | 2/2004 |
| EP | 1 426 063 | A2 | 6/2004 |
| EP | 1 568 397 | A1 | 8/2005 |
| EP | 1 239 920 | B1 | 5/2006 |
| JP | 3-30760 | | 2/1991 |
| JP | 2006 26443 | | 2/2006 |
| RU | 2 089 143 | C1 | 9/1997 |
| RU | 2 128 060 | C1 | 3/1999 |
| WO | WO 96/02059 | A1 | 1/1996 |
| WO | WO 98/15315 | A1 | 4/1998 |
| WO | WO 99/02219 | A1 | 1/1999 |
| WO | WO 99/04856 | A1 | 2/1999 |
| WO | WO 99/22812 | A1 | 5/1999 |
| WO | WO 99/24117 | A1 | 5/1999 |
| WO | WO 99/033515 | | 7/1999 |
| WO | WO 99/33515 | A2 | 7/1999 |
| WO | WO 01/43826 | A1 | 6/2001 |
| WO | WO 2007/056714 | A1 | 5/2007 |

OTHER PUBLICATIONS

U.S. Appl. No. 60/735,649, filed Nov. 10, 2005, Hermann et al.

Anbai, A. et al. Brachytherapy with Iridium-192 Thin Wire for Head and Neck Carcinoma. Jibi Inkoka, Tokeibu Geka (Otolaryngology—Head and Neck Surgery), 1998, vol. 70, No. 7, pp. 417-421. (In Japanese, Abstract only).

Armstrong, J.G. et al. The Use of a Prosthetic Tissue Expander to Displace Bowel from a Brachytherapy Implant Site. International Journal of Radiation Oncology, Biology, Physics, Dec. 1990, vol. 19, No. 6, pp. 1521-1523.

Balter, S. Endovascular Brachytherapy: Physics and Technology. Catheterization and Cardiovascular Diagnosis, 1998, vol. 45, No. 3, pp. 292-298.

Benitez, P.R. et al. Preliminary Results and Evaluation of MammoSite Balloon Brachytherapy for Partial Breast Irradiation for Pure Ductal Carcinoma in Situ: A Phase II Clinical Study. American Journal of Surgery, 2006, vol. 192, No. 4, pp. 427-433.

Diederich, C.J. et al. Direct-Coupled Interstitial Ultrasound Applicators for Simultaneous Thermobrachytherapy: A Feasibility Study. International Journal of Hyperthermia, May-Jun. 1996, vol. 12, No. 3, pp. 401-419.

Do, L. et al. LDR Brachytherapy Implants as a Boost in Early Stage Breast Cancer in Women with Cilastic Implants. In Proceedings of the American Brachytherapy Society, 27th Annual Meeting, 2006, vol. 5, No. 2, p. 95. (Abstract only).

Fukui, A. et al. Problems of Treatment Planning of Intracavitary Brachytherapy for Advanced Esophageal Cancer. Rinsho Hoshasen (Japanese Journal of Clinical Radiology), 1999, vol. 44, No. 8, pp. 981-984. (In Japanese, Abstract only).

Gildenberg, P.L. et al. Fractionated Brachytherapy: Catheter Insertion and Dosimetry. Stereotact. Funct. Neurosurg. 1994, vol. 63, Nos. 1-4, pp. 246-249.

Hirschberg, H. et al. An Indwelling Brachytherapy Balloon Catheter: Potential Use as an Intracranial Light Applicator for Photodynamic Therapy. Journal of Neuro-Oncolocy, Aug. 1999, vol. 44, No. 1, pp. 15-21.

Inakoshi H. et al. A New Radiotherapy Planning Program Using a New Double-Lumen Ballon Applicator for High-Dose-Rate Intracavitary Irradiation of Esophageal Cancer. Rinsho Hoshasen (Japanese Journal of Clinical Radiology), 1993, vol. 38, No. 5, pp. 565-569. (In Japanese, Abstract only).

International Search Report for PCT Application No. PCT/US2007/083672, International Filing Date, Nov. 5, 2007. Search Report mailed May 20, 2008.

International Search Report for PCT Application No. PCT/US06/45081, International Filing Date, Nov. 21, 2006, date of mailing Apr. 4, 2007.

Jani, S.K. et al. Dose Anisotropy Around an Au-198 Seed Source. Medical Physics, Jul.-Aug. 1989, vol. 16, No. 4, pp. 632-635.

Kubo, H.D. et al. Impact of Collimator Leaf Width on Stereotatic Radioosurgery and 3D Conformal Radiotherapy Treatment Plans. International Journal of Radiation Oncology Biology Physics, Jul. 1, 1999, vol. 44, No. 4, pp. 937-945.

Kuske, R.R. et al. Wide Volume Brachytherapy Alone for Select Breast Cancers: The Ten Year Experience of the Ochsner Clinic. International Journal of Radiation Oncology Biology Physics, 2000: vol. 48, No. 3; Suppl. 1, p. 2063. (Abstract only).

Malgieri, M. Relative Effects of Different Modalities of Brachytherapy on Late Responding Tissues and Tumours. Radiotherapy and Oncology, 1996, vol. 39, No. Sup. 1, p. 88. (Abstract only).

Marinello, G. et al. Comparative Dosimetry Between Iridium Wires and Seed Ribbons. International Journal of Radiation Oncology, Biology, Physics, Sep. 1985, vol. 11, No. 9, pp. 1733-1739.

Mazeron, J.J. et al. Treatment of Bladder Tumors by Iridium 192 Implantation. The Creteil Technique. Oncology (Netherlands), 1985, vol. 4, No. 2, pp. 111-119.

Muller-Runkel R. et al. Brachytherapy Implants with Differently Spaced Ir-192 Seeds: A Dosimetric Study. Radiology, Oct. 1987, vol. 165, No. 1, pp. 271-274.

Ogawa, K. et al. Intraluminal Brachytherapy Using a Balloon Applicator for Superficial Esophageal Carcinoma: Importance of Applicator Confirmation by Computed Tomography. Radiation Medicine, 1999, vol. 17, No. 5, pp. 399-401.

Pierquin, B. et al. Intracavitary Irradiation of Carcinomas of the Uterus and Cervix: The Cretail Method. International Journal of Radiation Oncology, Biology, Physics, Dec. 1988, vol. 15, No. 6, pp. 1465-1473.

Popowski, Y. et al. Intra-arterial $^{90}$Y Brachytherapy: Preliminary Dosimetric Study Using a Specially Modified Angioplasty Balloon. International Journal of Radiation Oncology Biology Physics, Oct. 1995, vol. 33, No. 3, pp. 713-717.

Rownd, J. Applicator Design and Dose Distributions. In Medical Physics Monograph, No. 31, pp. 797-804 (Madison, WI: Medical Physics Publishing, 2005).

Sealy, R. et al. The Treatment of Cancer of the Uvula and Soft Palate with Interstitial Radioactive Wire Implants. International Journal of Radiation Oncology, Biology, Physics, 1984, vol. 10, No. 10, pp. 1951-1955.

Xu, Z. et al. The Investigation of $^{32}$P Wire for Catheter-Based Endovascular Irradiation. Medical Physics, Nov. 1997, vol. 24, No. 11, pp. 1788-1792.

Yorozu, A. et al. Curative Radiotherapy with High-Dose-Rate Brachytherapy Boost for Localized Esophageal Carcinoma: Dose-Effect Relationship of Brachytherapy with the Balloon Type Applicator System. Radiotherapy and Oncology, May 1999, vol. 51, No. 2, pp. 133-139.

Zavgorodni, S.F. et al. Comparison of Three Simply Radiosurgery Techniques for Treating Elongated Lesions. Physica Medica, Apr.-Jun. 1999, vol. 15, No. 2, pp. 57-62.

* cited by examiner

BRACHYTHERAPY DEVICE HAVING SEED TUBES WITH INDIVIDUALLY-SETTABLE TISSUE SPACINGS

CROSS-REFERENCE TO RELATED APPLICATIONS

This application claims priority to U.S. Provisional Patent Application Ser. No. 60/864,288, entitled "Brachytherapy Device Having Seed Tubes With Individually-Settable Tissue Spacing," filed Nov. 3, 2006. This application is also related to U.S. patent application Ser. No. 11/305,437, entitled "Brachytherapy Apparatus," filed Dec. 16, 2005, and U.S. Continuation application Ser. No. 11/379,739, entitled "Brachytherapy Apparatus for Asymmetrical Cavities," filed Apr. 21, 2006 now abandoned. The contents of all of these applications are incorporated herein by reference in their entirety.

BACKGROUND

1. Field

This application relates to brachytherapy.

2. Description of Related Art

Brachytherapy is used in a variety of treatments. Often times, a high dose of radiation is needed. However, it may be difficult to apply a high dose to areas in need of treatment, without also causing damage to healthy tissue in the vicinity.

SUMMARY

A brachytherapy device may include a plurality of rods, each configured to move between a straightened position and a bowed position, the plurality of rods configured to collectively form a shaft while each rod is in the straightened position and to collectively form at least one cage while at least some of the rods are in the bowed position, at least some of the rods having lumens that are configured to receive and hold radioactive material. A brachytherapy device may further include a rotatable mechanism configured to cause at least some of the plurality of rods to move between the straightened position and the bowed position upon rotation of the rotatable mechanism.

A brachytherapy device may comprise a plurality of rods, each configured to move between a straightened position and a bowed position, the plurality of rods configured to collectively form a shaft while each rod is in the straightened position and to collectively form at least one cage while at least some of the rods are in the bowed position, at least some of the rods having lumens that are configured to receive and hold radioactive material, wherein some of the rods are configured to form a first cylinder while in the straightened position and the other rods are configured to form a second cylinder while in the straightened position that surrounds the first cylinder, whereby the plurality of rods are further configured such that at least a substantial portion of each the rod in the second cylinder lies between two rods within the first cylinder while in the straightened position.

A brachytherapy device may further comprise a plurality of rods, each configured to move between a straightened position and a bowed position, the plurality of rods configured to collectively form a shaft while each rod is in the straightened position and to collectively form at least one cage while at least some of the rods are in the bowed position, at least some of the rods having lumens that are configured to receive and hold radioactive material, wherein each rod has opposing longitudinal edges, each of which is configured to interlock with a longitudinal edge of a neighboring rod while in the straightened position.

A brachytherapy device may include a first and a second set of rods, at least some of the rods having lumens that are configured to receive and hold radioactive material. A brachytherapy device may further include a group expansion mechanism associated with the first set of rods and configure to collectively move the first set of rods in unison, each between a straightened position and a bowed position, the first set of rods configured to collectively form a shaft while each of the first set of rods is in the straightened position and to collectively form a cage while each of the first set of rods is in the bowed position. A brachytherapy device may further include a rod bowing mechanism associated with each of the second set of rods and configured to individually move each of the second set of rods between a straightened and a bowed position, the second set of rods configured to collectively form a shaft while each of the second set of rods is in the straightened position.

A brachytherapy device may include a plurality of rods configured to move between a straightened position and a bowed position, the rods configured to collectively form a shaft while each of the second set of rods is in the straightened position, at least some of the rods having lumens configured to receive and hold radioactive material. A brachytherapy device may further include a plurality of actuators, each associate with one of the rods and configured to cause the rod with which it is associated to move from the straightened position to the bowed position in incremental steps, each of the incremental steps being delineated by a ratchet mechanism.

These, as well as other components, steps, features, objects, benefits, and advantages, will now become clear from a review of the following detailed description of illustrative embodiments and the accompanying drawings.

BRIEF DESCRIPTION OF DRAWINGS

The drawings disclose illustrative embodiments. They do not set forth all embodiments. Other embodiments may be used in addition or instead. Details that may be apparent or that are unnecessary are also often omitted to save space or for more effective illustration. When the same numeral appears in different drawings, it is intended to refer to the same or like components or steps.

DETAILED DESCRIPTION OF ILLUSTRATIVE EMBODIMENTS

Illustrative embodiments are now discussed. Other embodiments may be used in addition or instead. Details that may be apparent or that are unnecessary are also often omitted to save space or for more effective presentation.

Figure 1:
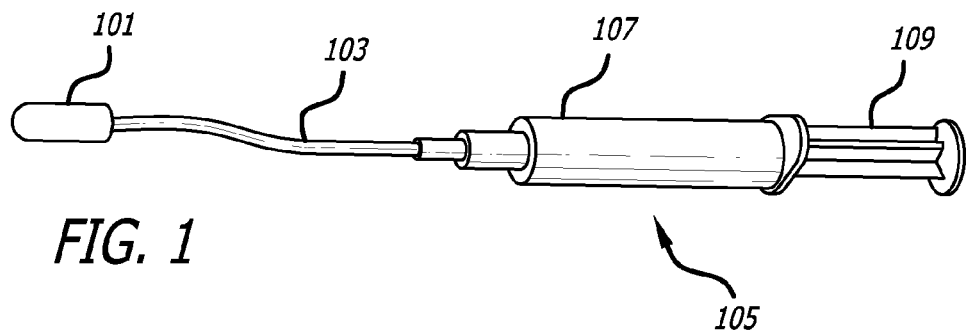
FIG. 1 illustrates a pre-expander balloon apparatus.

FIG. 1 illustrates a pre-expander balloon apparatus. As shown in FIG. 1, the pre-expander balloon apparatus may include a balloon 101—illustrated in a deflated state—an inflation tube 103, and an inflation applicator 105.

The balloon 101 may be configured to inflate with gas or fluid. The inflation tube 103 may be configured to carry the gas or fluid from the inflation applicator 105 to the balloon 101. The inflation applicator 105 may include a reservoir cylinder 107 and a plunger 109 which may contain the gas or fluid. Any type of gas or fluid may be used. In one embodiment, saline may be used.

Figure 2:
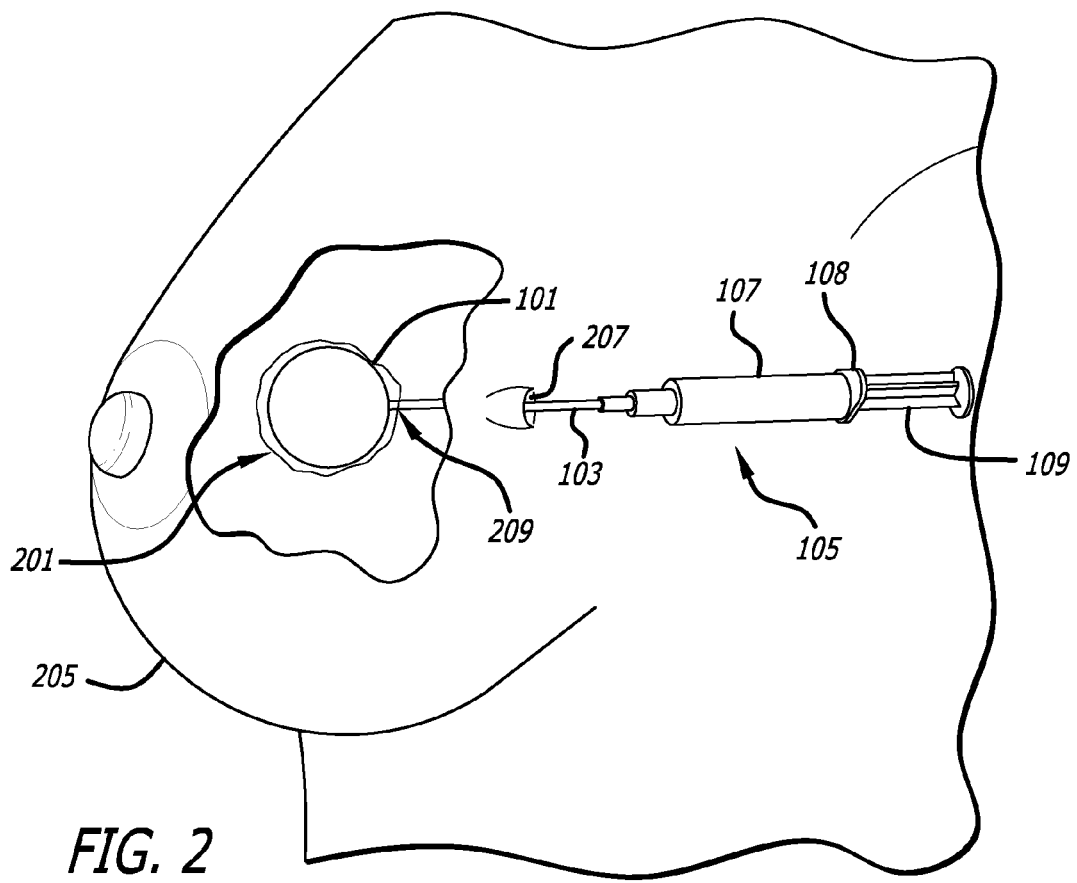
FIG. 2 illustrates the pre-expander balloon apparatus inserted into a cavity of a breast and inflated.

FIG. 2 illustrates the pre-expander balloon apparatus inserted into a cavity 201. The cavity 201 may be a cavity in any area of a body, such as in a breast 205. It may be a cavity formed by the extraction of a cancerous tumor or that exists for any other reason.

The balloon 101 while in its deflated state may be inserted through an opening 207 in the skin surface of the breast 205 and into the cavity 201. The opening 207 and the pathway to the cavity may have been created during the resection of the tumor or at any other time. Once in the cavity, the balloon 101 may be expanded by applying force to the plunger 109 while retaining a grasp of tabs 108 on the reservoir cylinder 107.

The balloon 101 may be inflated until it substantially fills the cavity. An X-ray or CT scan may be used to determine when this point has been reached.

The distance between the opening 207 on the skin surface and the initial entry point 209 to the cavity 201 may be measured. For this purpose, the inflation tube 103 may be marked with gradations. The gradation that is closest to the opening 207 on the inflation tube 103 may be noted and this measurement may be recorded for later use.

The inflation applicator 105 may be detached from the inflation tube 103 and the inflation tube 103 may be sealed so that the balloon 101 remains inflated. The inflated balloon 101 may be left within the cavity 201 until the patient is ready for radiation treatment.

When the patient is ready for radiation treatment, the inflation tube 103 may be reopened at its distal end, thus allowing the balloon 101 to deflate. The balloon 101 and the inflation tube 103 may then be removed from the breast 205.

Figure 3:
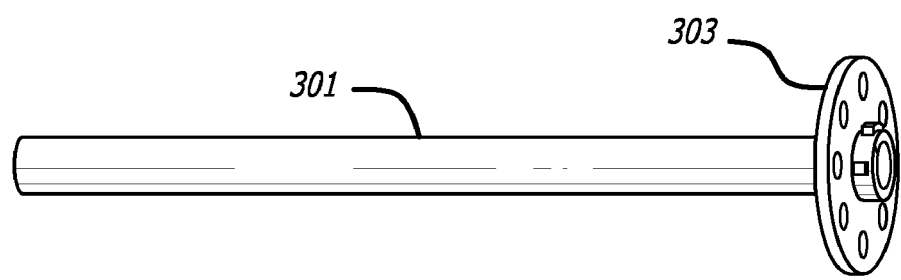
FIG. 3 illustrates a sleeve having a flanged end.

FIG. 3 illustrates a sleeve 301 having a flanged end 303. Before use, the length of the sleeve 301 may be trimmed to the initial depth of the cavity 201. As explained above, this measurement may have already been made by noting the gradation on the inflation tube 103 that was at the surface of the skin. It may have been made by other means or may be made now.

Figure 4:
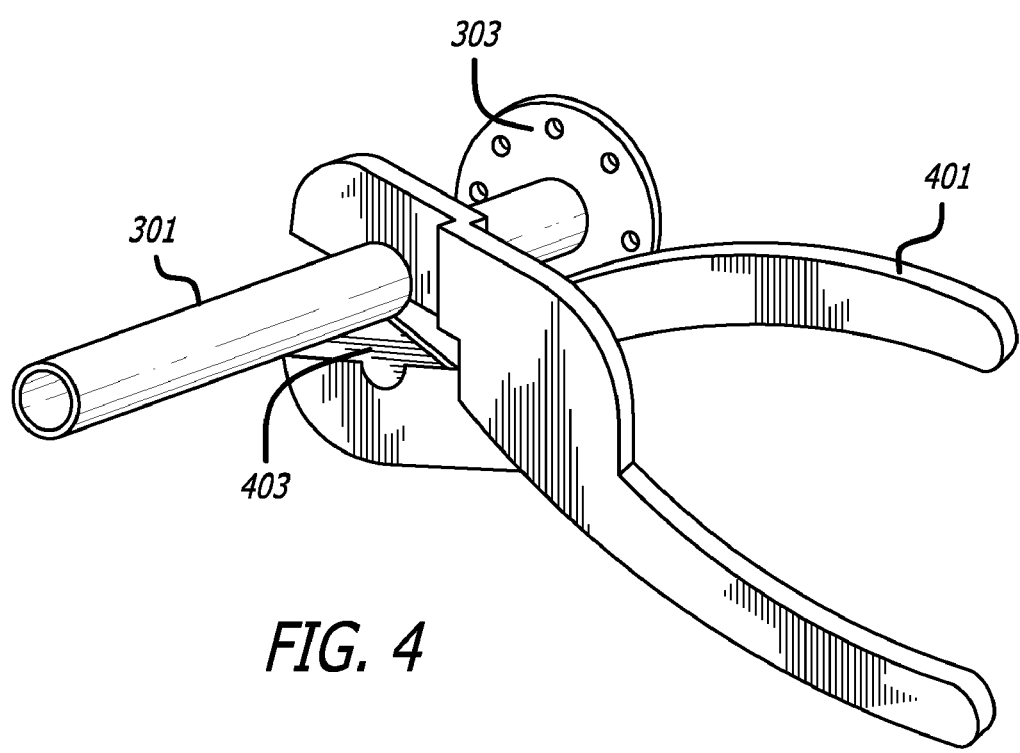
FIG. 4 illustrates the sleeve being cut by a cutting tool.

FIG. 4 illustrates the sleeve 301 being cut by a cutting tool 401. The cutting tool 401 may have a cutting blade 403 and may be positioned to cut the sleeve 301 at a length that is approximately equal to the initial depth of the cavity within the breast 205.

Figure 5:
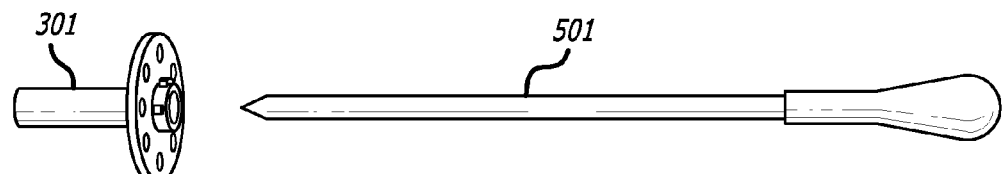
FIG. 5 illustrates a trocar being inserted into the sleeve.

FIG. 5 illustrates a trocar 501 being inserted into the sleeve 301.

Figure 6:
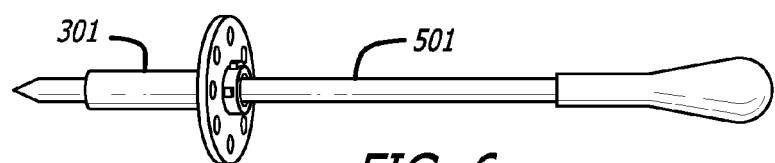
FIG. 6 illustrates the trocar after it has been inserted through the sleeve.

FIG. 6 illustrates the trocar 501 after it has been inserted through the sleeve 301.

Figure 7:
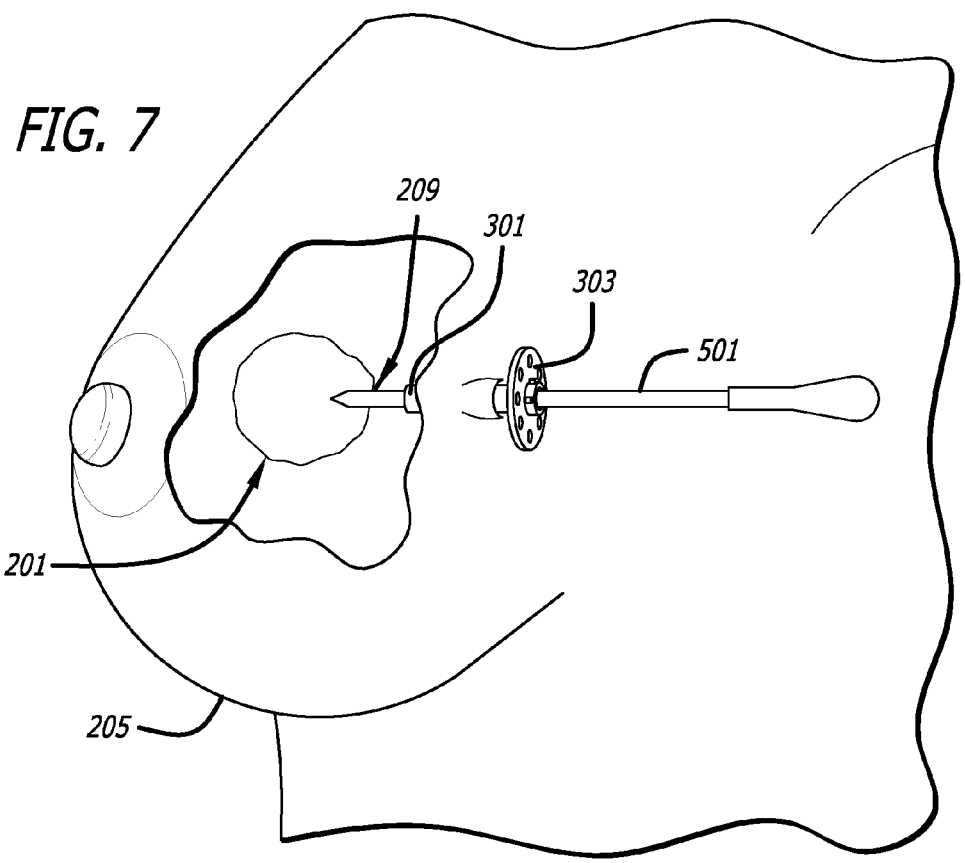
FIG. 7 illustrates the trocar and sleeve after they have been inserted into the resected cavity of the breast.

The trocar 501 and the sleeve 301 may be inserted into the cavity 201 of the breast 205, as shown in FIG. 7. The sleeve 301 may be pushed into the breast until its flanged end abuts the surface of the skin and its proximate end reaches the initial entry point 209 into the cavity.

Figure 8:
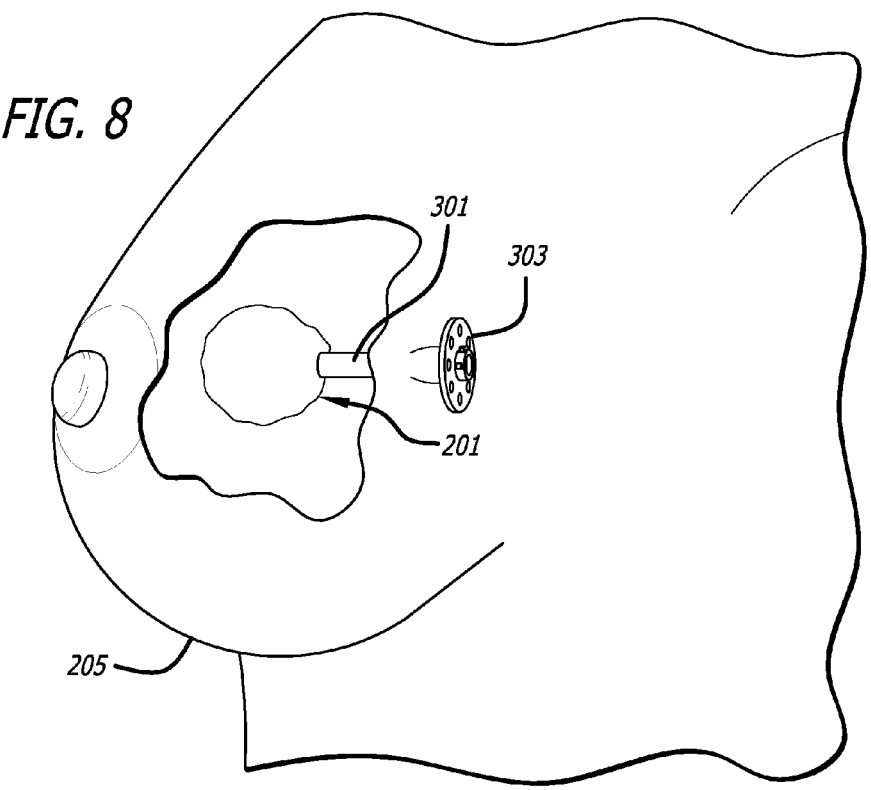
FIG. 8 illustrates the sleeve inserted into the breast after the trocar has been removed.

FIG. 8 illustrates the sleeve 301 inserted into the breast 205 after the trocar 501 has been removed. The flanged end 303 of the sleeve 301 may be sutured to the breast at this time.

Figure 9:
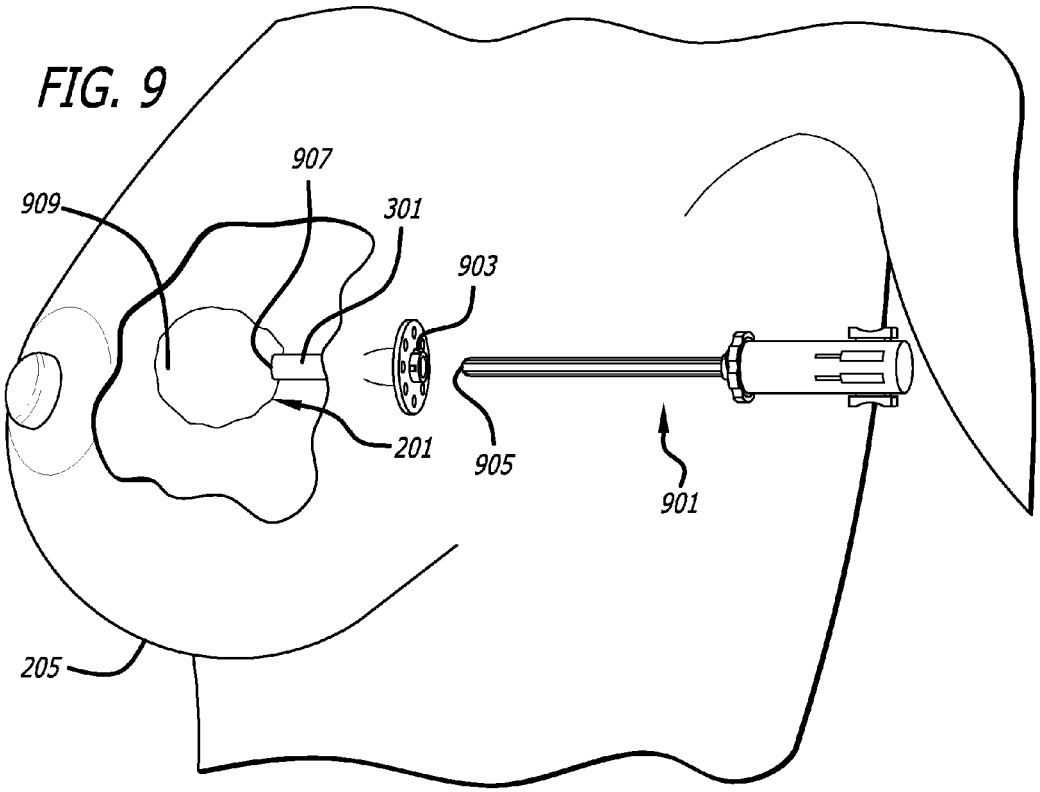
FIG. 9 illustrates a tube apparatus being inserted into a distal end of the sleeve.

FIG. 9 illustrates a tube apparatus 901 being inserted into a distal end 903 of the sleeve 301. The tube apparatus 901 may continue to be inserted into the sleeve 301 until its proximate end 905 passes through the proximate end 907 of the sleeve 301 and is stopped from further free movement by the opposite end 909 of the cavity 201.

Trimming the sleeve 301 to the initial depth of the cavity 201 and inserting the tube apparatus 901 into the cavity 201 until its proximate end 905 engages the opposite end 909 of the cavity 201 may cause the tube apparatus 901 to protrude beyond the proximate end 907 of the sleeve 301 by an amount that is approximately equal to the diameter of the cavity 201 and to be approximately centered within the cavity 201. In this way, a single sized tube apparatus 901 may be used to treat cavities of varying size, as will become apparent from the discussion below.

Figure 10:
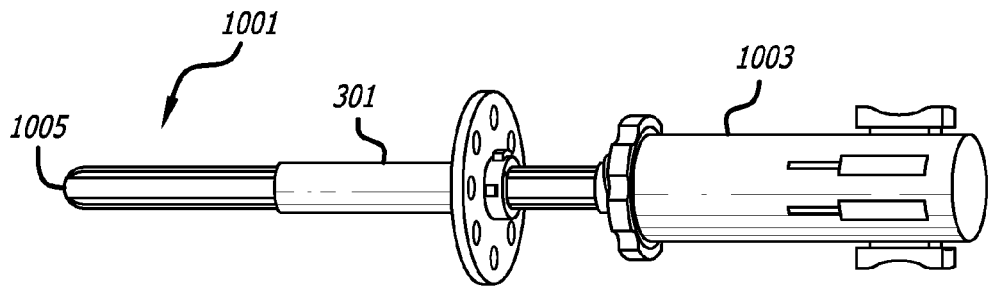
FIG. 10 is an enlarged view of the tube apparatus.

FIG. 10 is an enlarged view of the tube apparatus 901. The tube apparatus 901 may include a set of tubes 1001 positioned within the sleeve 301 and attached to a handle 1003.

The set of tubes 1001 may include any number of tubes bundled together. The proximate ends 1005 of the tubes 1001 may be bound together using any means, such as glue or an ultrasonic bond.

The tubes 1001 may be made of any material, including material that is normally straight, but resiliently flexes after longitudinal compression. Plastic or any other type of material may be used. A central lumen may or may not be provided within one, some or all of the tubes 1001.

The tubes 1001 may be of any number. Twelve will be discussed. A different number, such as 4, 5, 6, 7, 8, 9, 10, 11, 13, 14, 15, 16, etc. may be used instead.

Figure 11:
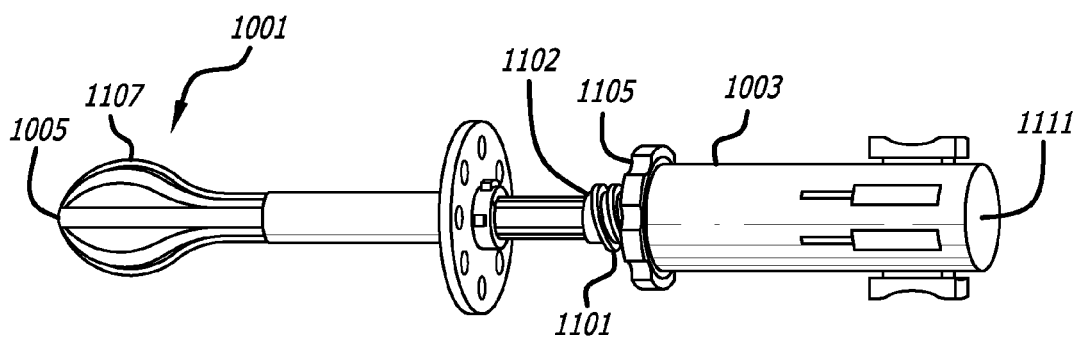
FIG. 11 illustrates the tube apparatus with its outer tubes partially expanded.

FIG. 11 illustrates the tube apparatus with its outer tubes 1107 partially expanded. The outer tubes 1107 constitute an outer portion of the tubes 1001.

A gear 1105 may mesh with threads 1101 on a collar 1102 that may be attached to distal ends of the outer tubes 1107. A rod 1109 may run through the center of the tubes 1001 and may be attached at its proximate end to the proximate end 1005 of the tubes 1001 and at its distal end to an end 1111 of the handle 1003. Any means may be used to effectuate this attachment, such as glue or ultrasonic bonding.

When the gear 1105 is rotated with respect to the handle 1003, this may cause the collar 1102 to move laterally away from the handle 1003 and to apply a longitudinal compressive force to the outer tubes 1107, thus causing them to expand in unison as show in FIG. 11.

Figure 12:
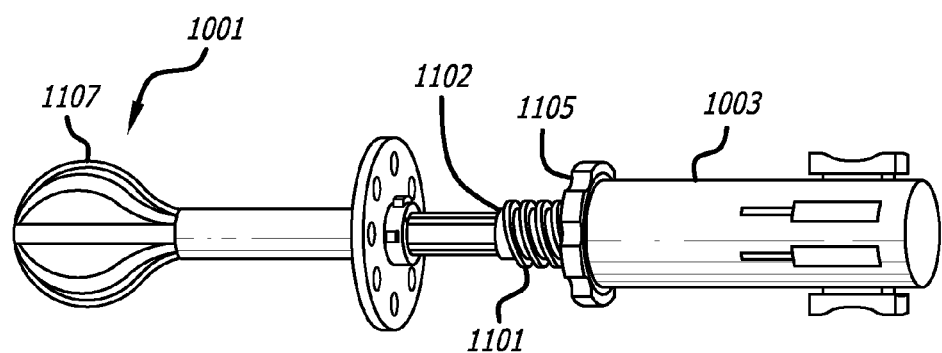
FIG. 12 illustrates the tube apparatus with the outer tubes more fully expanded.

FIG. 12 illustrates the tube apparatus the outer tubes 1107 more fully expanded. As shown in FIG. 12, the collar 1102 has been separated even further from the handle 1003 by continued rotation of the gear 1105 with respect to the handle 1003. This relative rotation may continue until the outer tubes 1107 substantially fill the cavity 201 in the breast 205. During some procedures, the rotation may be halted before this point is reached. During other procedures, the rotation may continue past this point.

Figure 13:
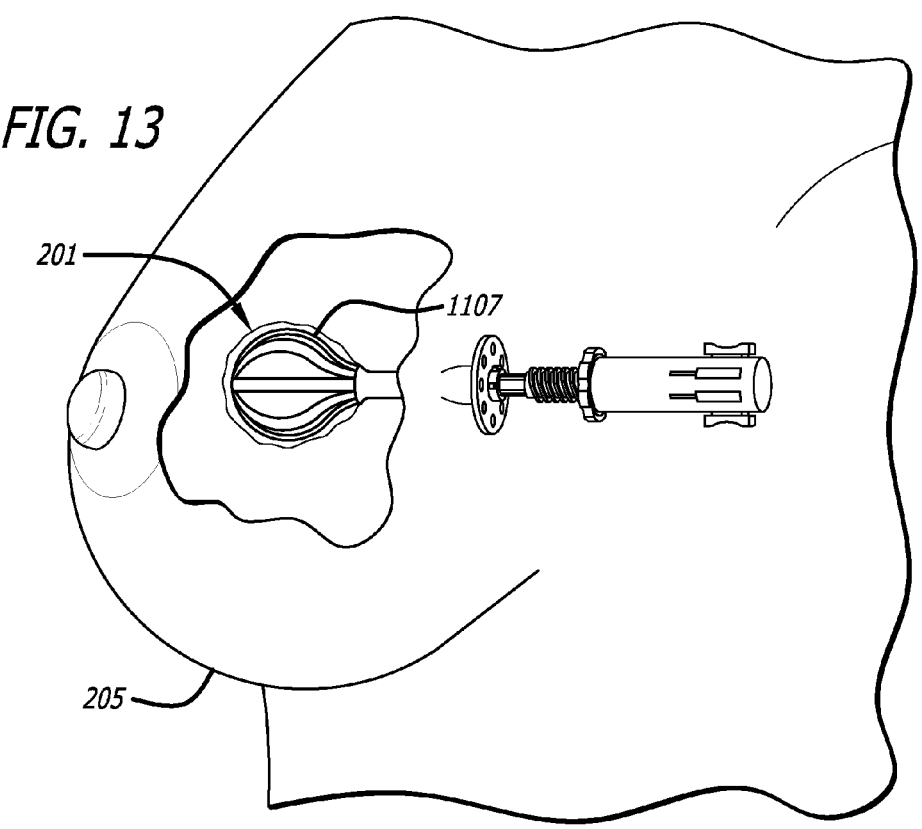
FIG. 13 illustrates the tube apparatus with the outer tubes expanded within the cavity in the breast.
Figure 14A:
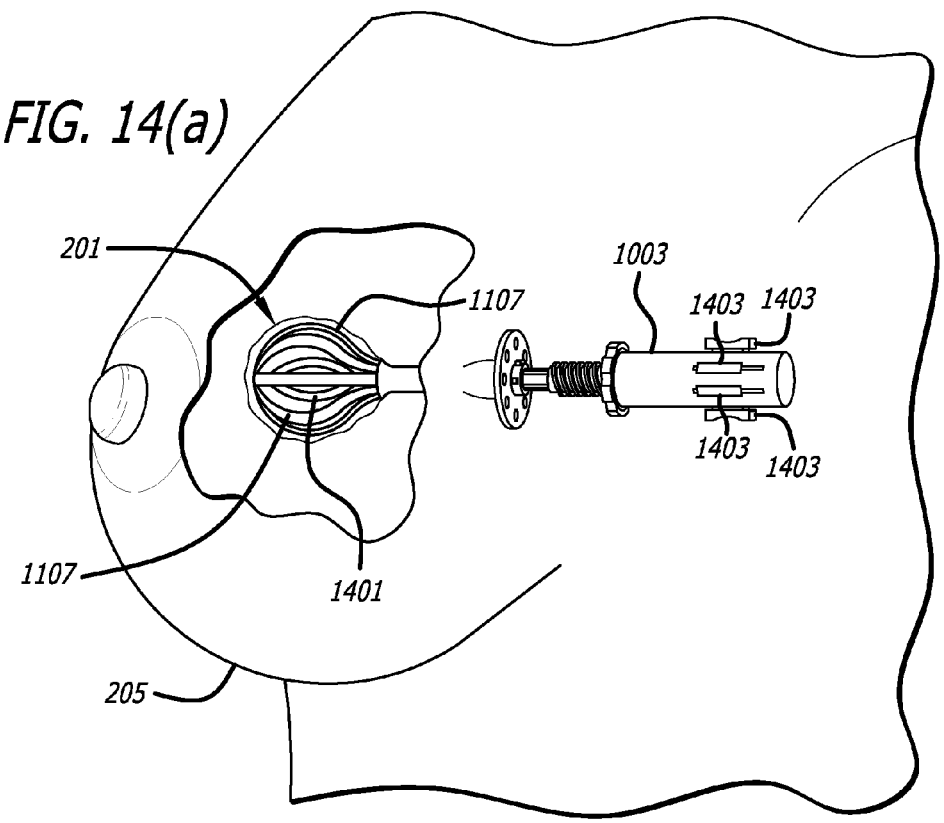
FIG. 14(a) illustrates the tube apparatus with the outer tubes expanded and with a set of inner tubes individually expanded within the cavity in the breast.
Figure 14B:
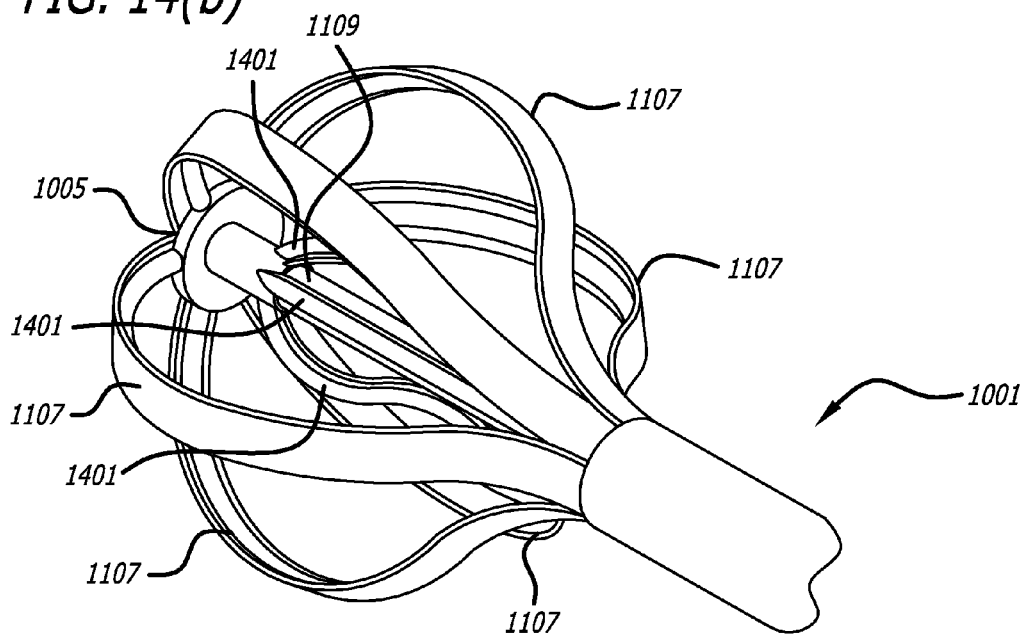
FIG. 14(b) is an enlarged perspective view of the proximate end of the tube apparatus.
Figure 14C:
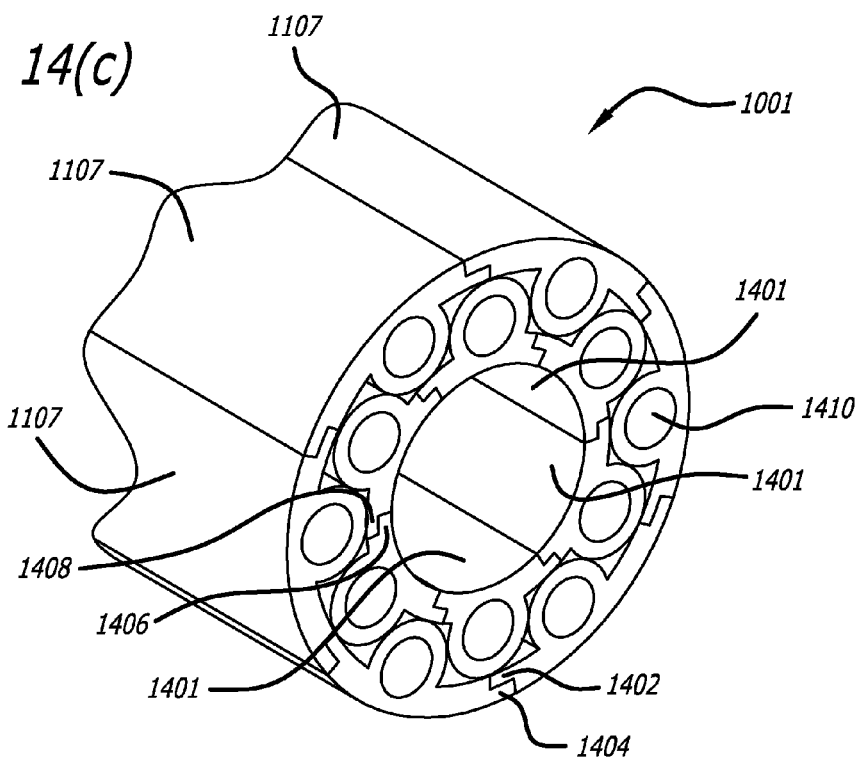
FIG. 14(c) is an enlarged perspective view of the distal end of tubes in the tube apparatus.
Figure 14D:
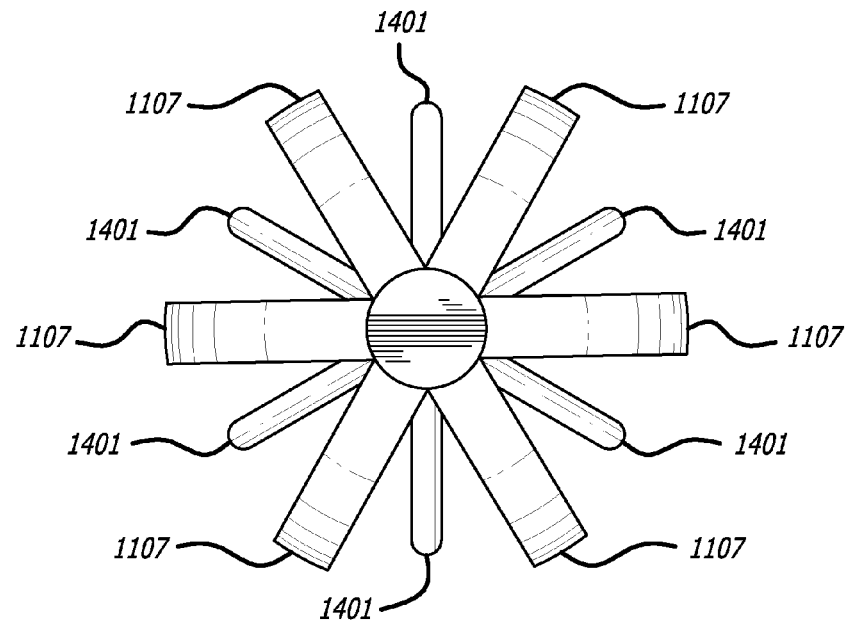
FIG. 14(d) illustrates an end view of the expanded inner and outer tubes.

FIG. 13 illustrates the tube apparatus with the outer tubes 1107 expanded within the cavity 201 in the breast 205. An X-ray or CT scan may be taken to verify that the outer tubes 1107 have been expanded to the desired amount and/or to provide information about adjustments that may be needed.

The number of the outer tubes 1107 may vary. Six are illustrated in FIG. 13. A different number may be used, such as 3, 4, 5, 7, or 8. The outer tubes 1107 may be oriented so that they are evenly distributed around the perimeter of the rod 1109, or they may be distributed in an uneven manner.

FIG. 14(*a*) illustrates the tube apparatus with the set of outer tubes 1107 expanded and with a set of inner tubes 1401 individually expanded within the cavity 20. Thumb sliders 1403 may each be separately attached to one of the inner tubes 1401. Each of the thumb sliders 1403 may be slid forward with respect to the handle 1003, causing longitudinal compression of the inner tube to which it is attached. This may cause the inner tube to bend outwardly. The amount of the bending may be a function of the degree to which the thumb slider is slid forward.

Each of the thumb sliders 1403 may include a ratchet or other type of mechanism that prevents the thumb slider from retreating, unless urged to do so by thumb pressure in the opposite direction.

Any number of inner tubes may be used for the set of inner tubes 1401. Six are illustrated in FIG. 14(*a*). A different number may be used, such as 1, 2, 3, 4, 5, 7, or 8.

As illustrated in FIG. 14(*a*), the outer tubes 1107 may surround the inner tubes 1401. In turn, the inner tubes 1107 may surround the rod 1109. These surrounding relationships may also exist when the tubes 1001 are in their uncompressed positions illustrated in FIG. 10. In another embodiment, the outer tubes 1107 and the inner tubes 1401 may all be at approximately the same radial position from the rod 1109 when in the uncompressed position shown in FIG. 10.

The outer tubes 1107 may be equal in number to the inner tubes 1401, as illustrated in FIG. 14(*a*). There may instead be more outer tubes than inner tubes or less.

The amount of bowing in each of the inner tubes 1401 that is caused by the sliding of its respective thumb slider may vary from procedure to procedure. The criteria that is employed for determining the amount may also vary.

During some procedures, all of the inner tubes 1401 may initially be bowed in the same amount in accordance with predetermined information, such as a formula, algorithm, or specification. This predetermined information may be dependent upon the particular patient and his or her situation. Alternately, it may be patient independent.

After initially bowing each of the inner tubes 1401 to this predetermined amount, adjustments may be made to one or more of the inner tubes 1401 to protect healthy tissue and/or to increase the dose to certain areas of the cavity 201. For example, the bowing of one or more of the inner tubes 1401 may be individually reduced by moving its respective thumb slider backwards so as to better protect healthy tissue in its vicinity, such as skin, a lung or the heart. Similarly, the bowing of one or more of the inner tubes 1401 may be individually increased by moving its respective thumb slider forwards so as to apply a greater dose to tissue in its vicinity.

FIG. 14(*b*) is an enlarged perspective view of the proximate end of the tube apparatus. It reveals details of the outer tubes 1107, the inner tubes 1401, the rod 1109, and the proximate end 1005.

FIG. 14(*c*) is an enlarged perspective view of the distal end of the tubes 1001 before they are inserted into the handle 1003. It reveals details of interlocking flanges between each of the outer tubes 1107, such as interlocking flanges 1402 and 1404, and between each of the inner tubes 1401, such as interlocking flanges 1406 and 1408. These interlocking flanges allow each of the tubes to slide separately with respect to its neighbors, while minimizing leaks. FIG. 14(*c*) also illustrates lumens that may run though the approximate center of each of the tubes 1001, such as lumen 1410. It also illustrates nesting between the inner tubes 1401 and the outer tubes 1107. This nesting may allows the outer tubes 1107 to slide longitudinally with respect to the inner tubes 1401.

FIG. 14(*d*) is an end view of the expanded inner tubes 1401 and outer tubes 1107. As illustrated in FIG. 14(*d*), each of the outer tubes 1107 may be bowed to the same degree and in an amount that is greater than the bowing of each of the inner tubes 1401. Although the bowing of each of the inner tubes 1401 is illustrated as being substantially the same in FIG. 14(*d*), there may be substantial variation among the bowing of each of the inner tubes 1401, as discussed above.

Figure 15:
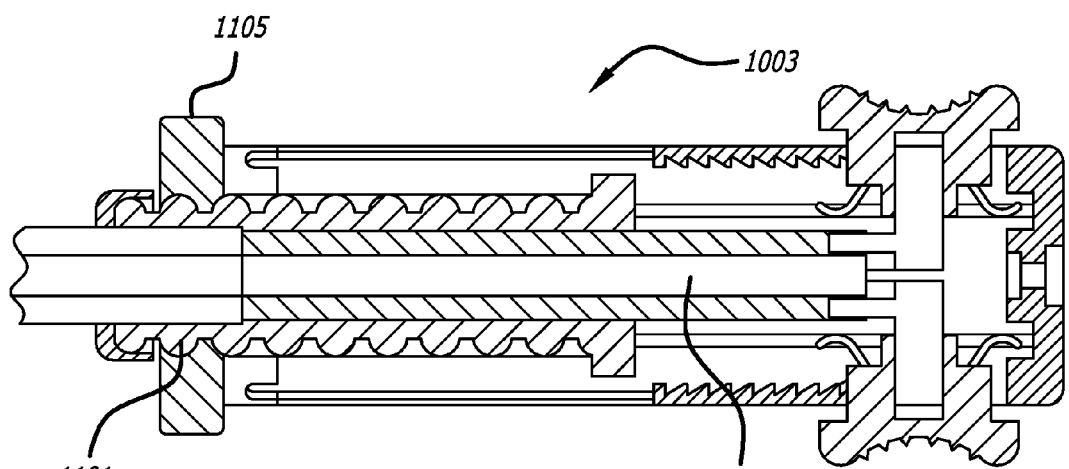
FIG. 15 illustrates a cross-section of a handle of the tube apparatus.

FIG. 15 illustrates a cross-section of the handle 1003.

Figure 16:
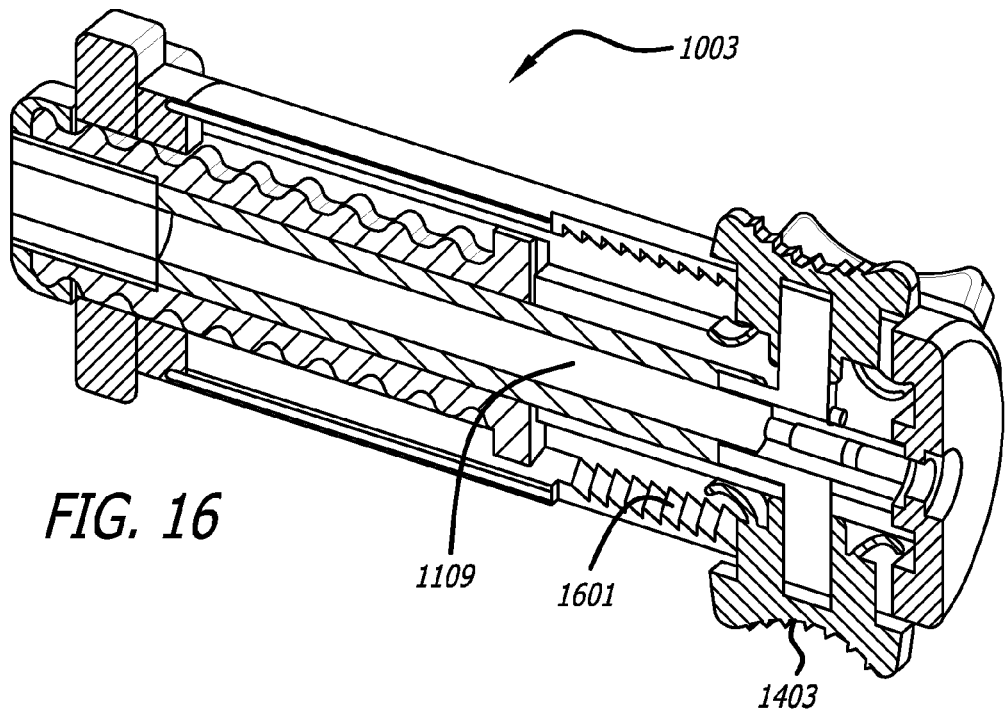
FIG. 16 illustrates a perspective view of the cross-section of the handle.

FIG. 16 illustrates a perspective view of the cross-section of the handle 1003 shown in FIG. 15. As shown in FIG. 16, ratchet teeth 1601 may cooperate with one of the thumb sliders 1403 to lock it in position after forward movement.

Figure 17:
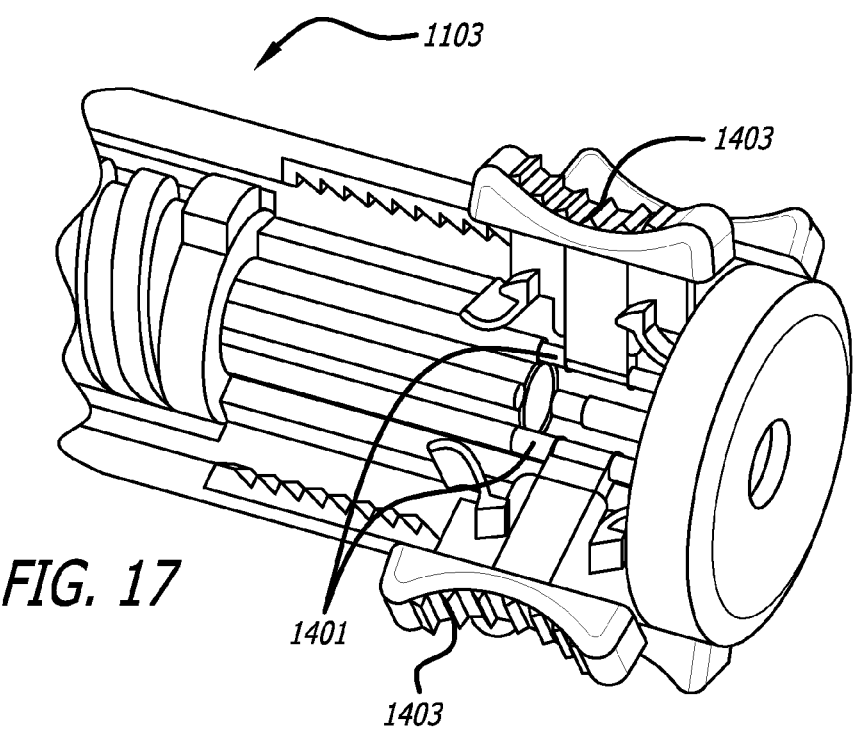
FIG. 17 illustrates an enlarged perspective view of the cross-section of the handle.

FIG. 17 is an enlarged perspective view of the cross-section of the handle 1003. FIG. 17 illustrates further details, including the interlocking relationship between each of the thumb sliders 1403 and the inner tube to which it applies longitudinal compressive force.

Figure 18:
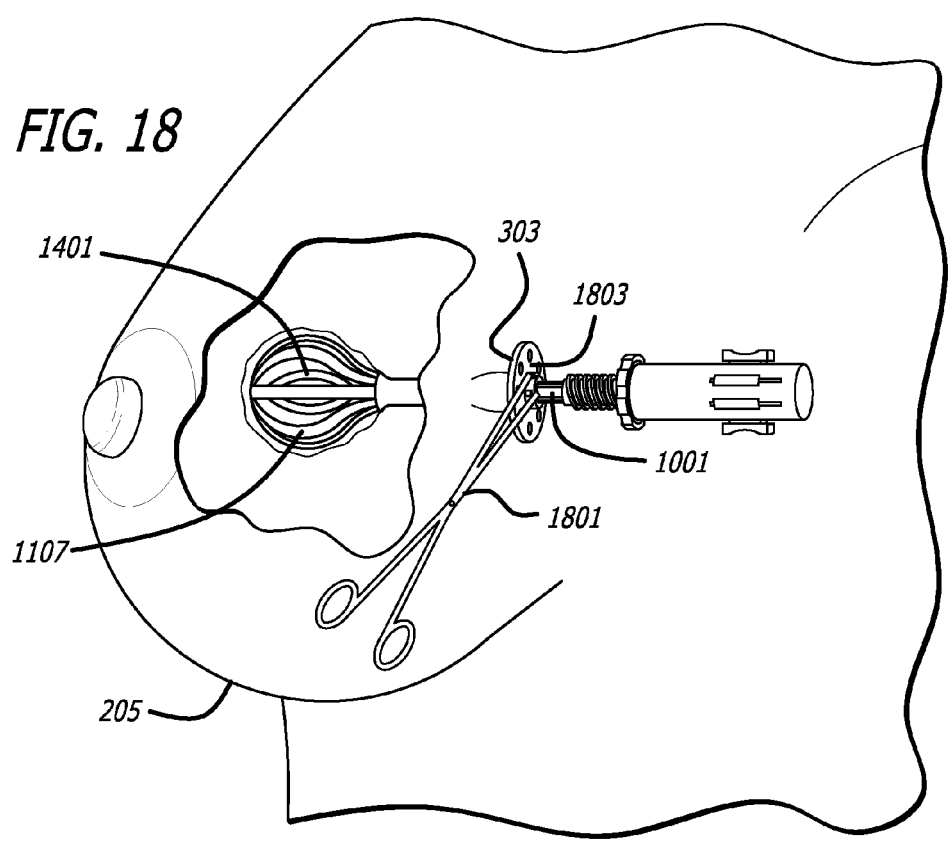
FIG. 18 illustrates a hemostat being used to lock the tubes in their expanded positions.

FIG. 18 illustrates a hemostat 1801 being used to lock the tubes 1001 in their bowed positions. A locking clamp 1803 may surround the tubes 1001 at the flanged end 303. Closure of the hemostat 1801 may cause the locking clamp 1803 to compress the tubes 1001 at this location, thus retaining their bowed positions.

Figure 19:
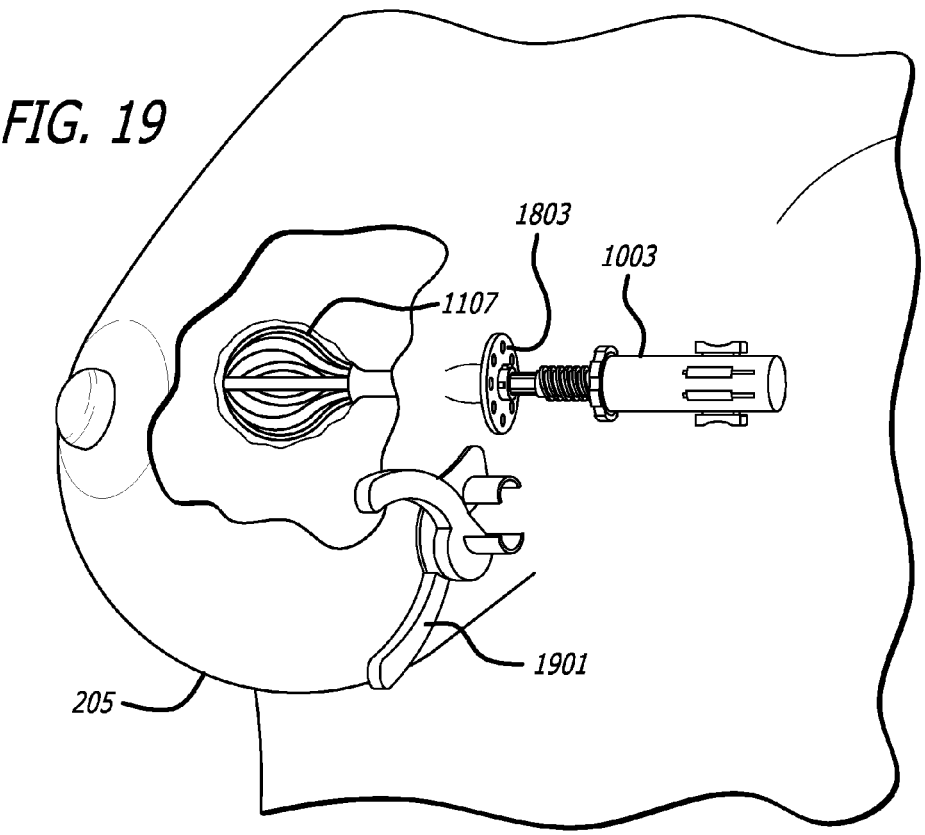
FIG. 19 illustrates the handle being cut from the tubes by a cutting tool.

FIG. 19 illustrates the handle 1103 being cut from the tubes 1001 by a cutting tool 1901. A cutting blade of the cutting tool 1901 may be positioned just beyond the distal end of the locking clamp 1803 and pressed against the tubes 1001.

Figure 20:
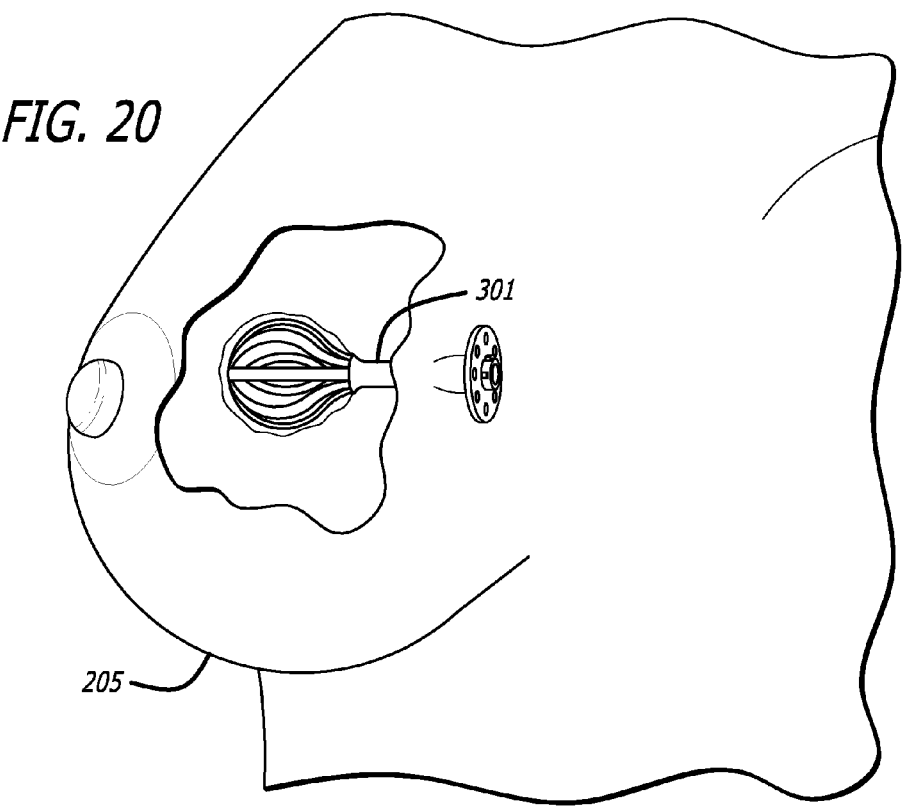
FIG. 20 illustrates the tubes while locked and after being separated from the handle.

FIG. 20 illustrates the tubes 1001 while locked and after having been separated from the handle 1103.

Figure 21:
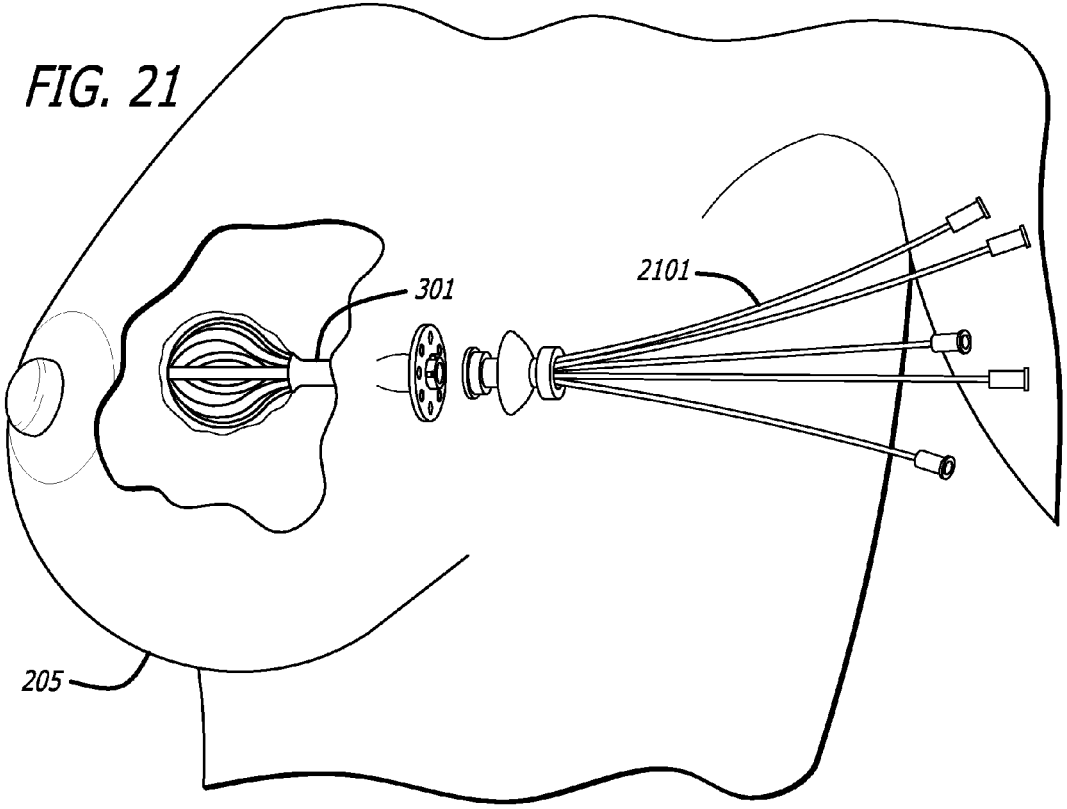
FIG. 21 illustrates an adapter being positioned for attachment to the sleeve.

FIG. 21 illustrates an adaptor 2101 being positioned for attachment to the sleeve 301. The adaptor 2101 may be any type of adaptor that may be configured to function with any type afterloader.

Figure 22:
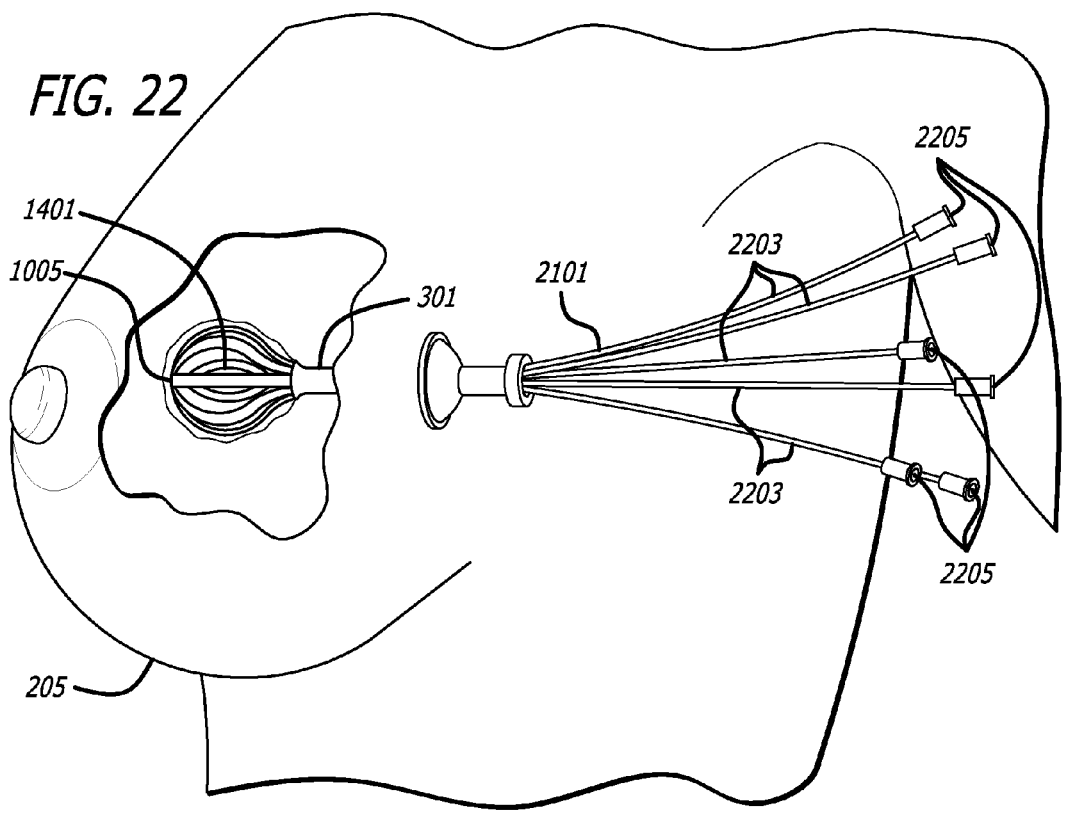
FIG. 22 illustrates the adapter attached to the sleeve.

FIG. 22 illustrates the adaptor 2101 attached to the sleeve 301. Any type of snap or interlocking device may be used for this purpose.

The adaptor 2101 may include a plurality of adapter tubes 2203. Each of the adapter tubes 2203 may be joined at the juncture between the adaptor 2101 and the sleeve 301 to one of the inner tubes 1401 so as to create a continuous central lumen from the distal ends 2205 of each of the adapter tubes 2203 to the proximate end 1005 of the inner tubes 1401.

The distal ends 2205 may be coupled to any type of afterloader. The afterloader may be configured to inject one or more strands, each containing one or more radioactive seeds, into the distal end of one or more of the adapter tubes 2203 and into one or more of the inner tubes 1401. The precise position of each radioactive seed within each of the inner tubes 1401 may be regulated by the afterloader, as well as the dwell time at each position.

The afterloader may be programmed to cause a single radioactive seed within a single strand to be sequentially injected into one or more of the inner tubes 1401 at one or more specified locations for one or more specified dwell times. Any type or combination of types of radiation treatment may be employed.

After completion of the radiation treatment, the adaptor 2101 may be detached from the sleeve 301 and a cap may be placed on the distal end of the sleeve 301 to protect it.

Figure 23:
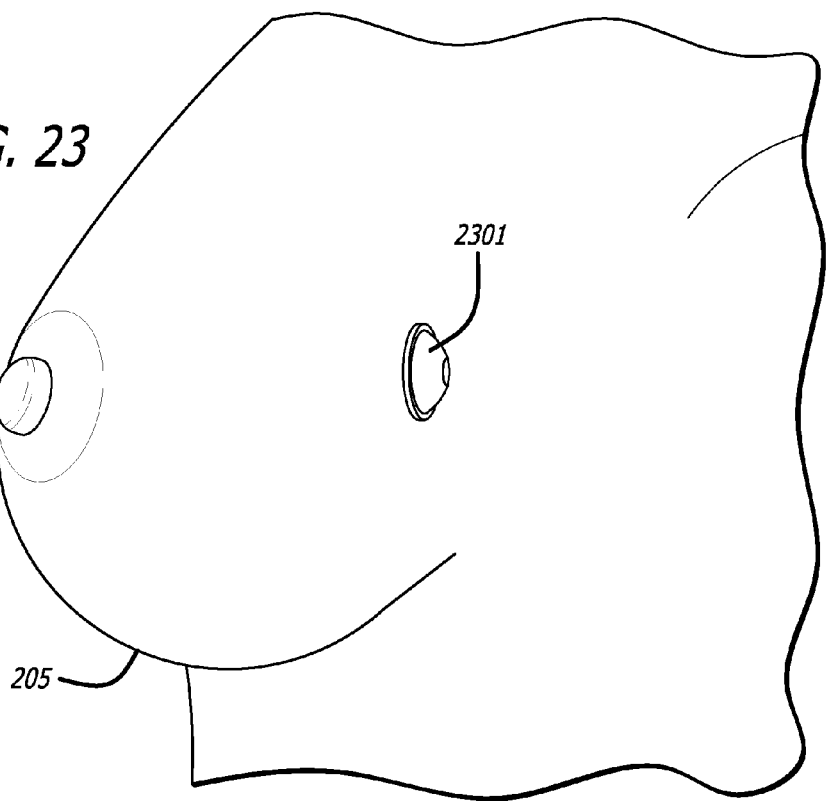
FIG. 23 illustrates a cap attached to the distal end of the sleeve.

FIG. 23 illustrates a cap 2301 attached to the distal end of the sleeve 301. The cap 2301 may remain attached until the next treatment is administered. At this time, the cap 2301 may be removed and the process described above in connection with FIGS. 21 and 22 may be repeated in the same or in a different way.

Figure 24:
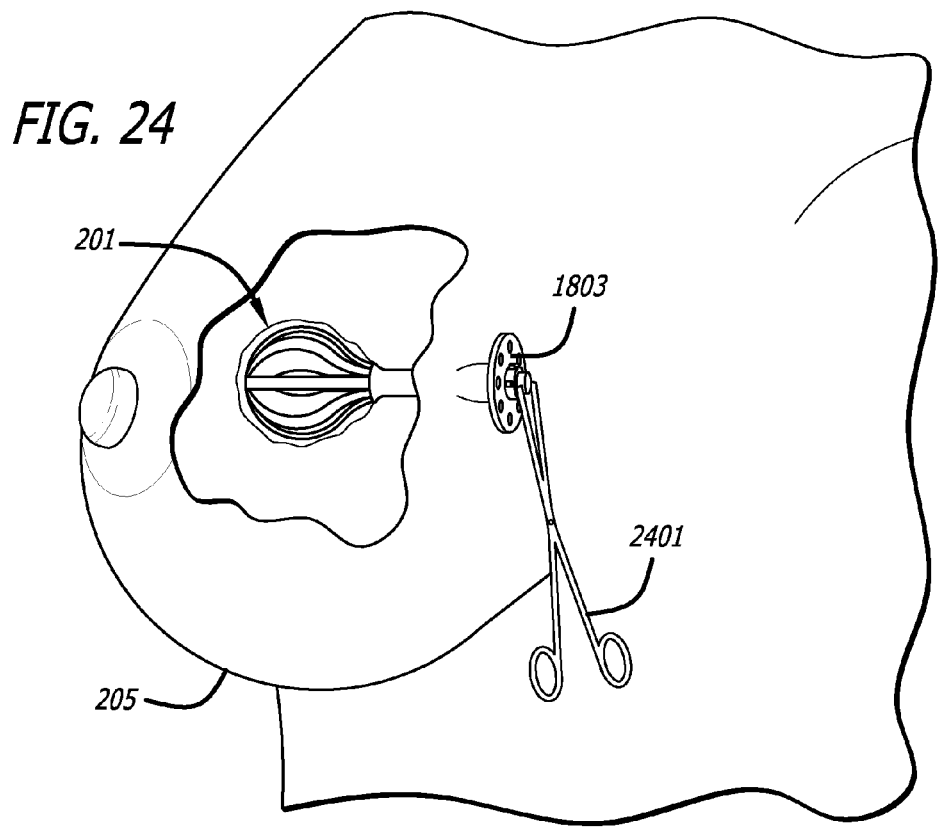
FIG. 24 illustrates a hemostat being used to unlock the tubes.

After one or more radiation treatments, the tube apparatus that is shown in FIG. 21 may be removed. FIG. 24 illustrates the hemostat 2401 being used to unlock the locking clamp 1803. After the locking clamp 1803 is unlocked, the tubes may naturally tend to go back to their straightened position.

Figure 25:
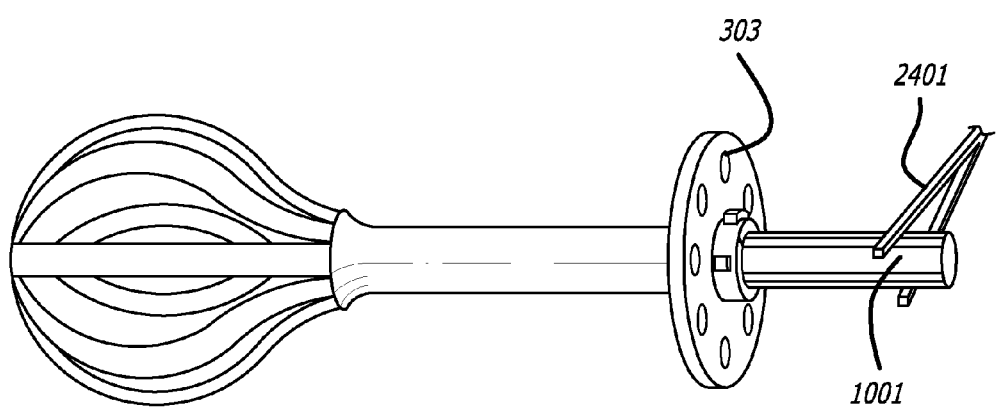
FIG. 25 illustrates the hemostat being used to straighten the tubes.

FIG. 25 illustrates the hemostat 2401 being used to straighten the tubes 1001. As shown in FIG. 25, the tubes may not fully straighten on their own. By pulling them distally with the hemostat 2401, they may be completely straightened.

Figure 26:
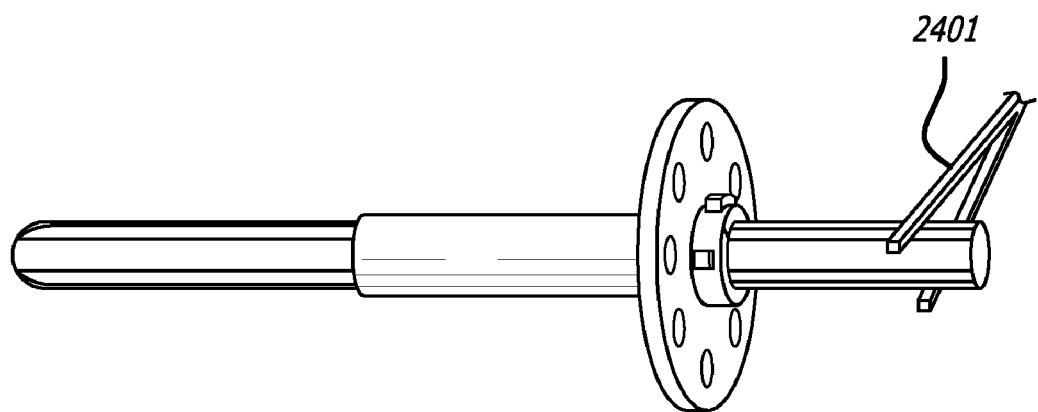
FIG. 26 illustrates the hemostat being used to grab the tubes after they have been straightened.

FIG. 26 illustrates the hemostat 2401 being used to grab the tubes 1001 after they have been completely straightened.

Figure 27:
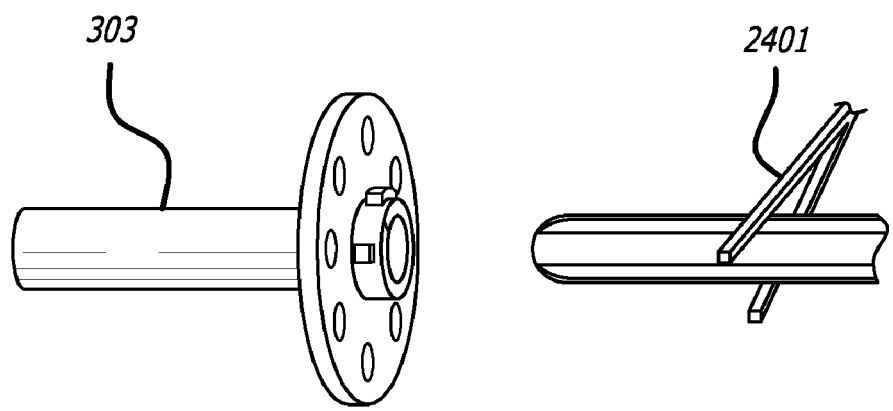
FIG. 27 illustrates the straightened tubes being removed from the sleeve by the hemostat.

FIG. 27 illustrates the straightened tubes 1001 being removed from the sleeve 301 by the hemostat 2401. Thereafter, the sleeve 301 may be removed from the breast.

Figure 28:
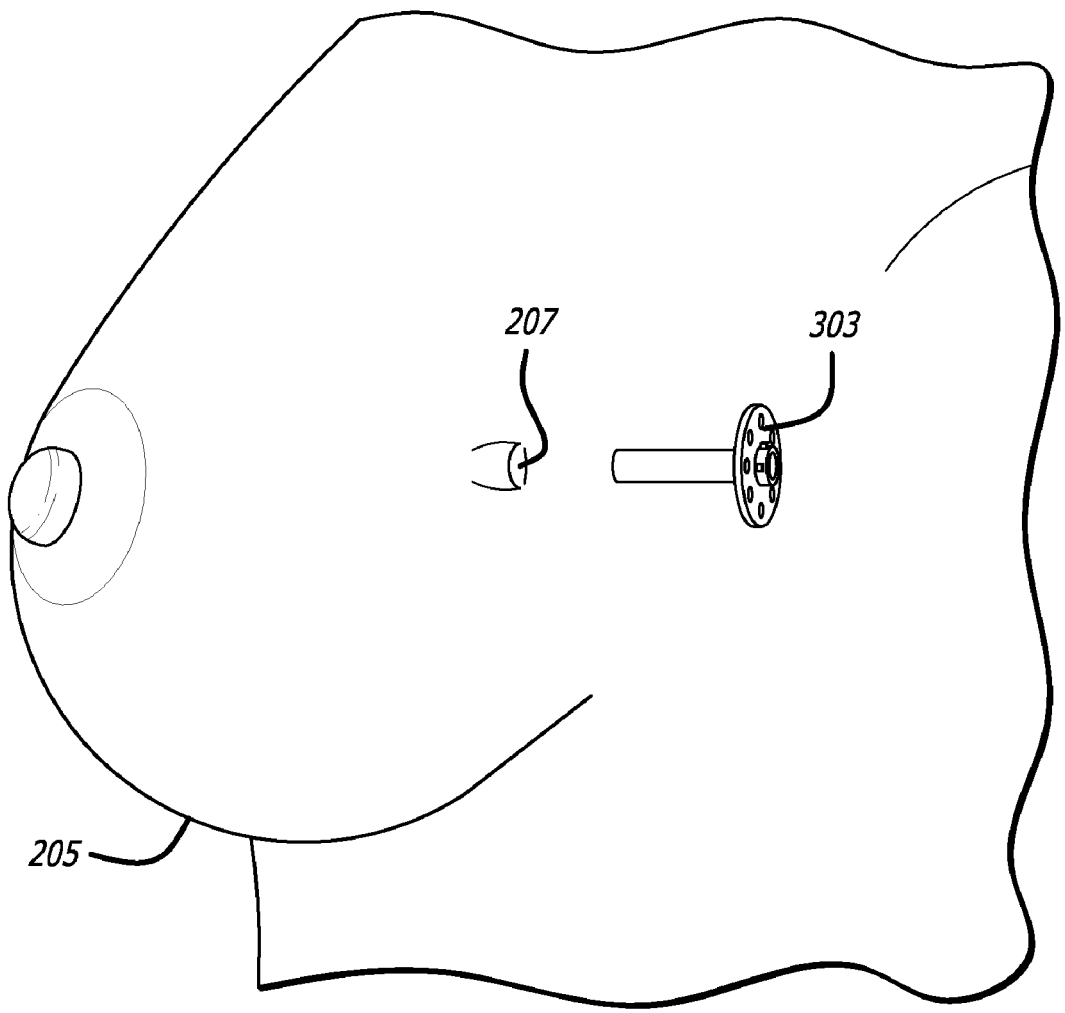
FIG. 28 illustrates the sleeve being removed from the breast.

FIG. 28 illustrates the sleeve 301 being removed from the breast 205. The opening 207 in the breast 205 may then be sutured and allowed to heal.

The components, steps, features, objects, benefits and advantages that have been discussed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

For example, the device and procedures that have been described may be used in conjunction with brachytherapy treatments for tissue other than breast tissue, such as for the brain and/or the prostate. Although a strand with one or more radioactive seeds has thus-far been described as being inserted into the inner tubes 1401, one or more strands containing one or more seeds may in addition or instead be inserted into a lumen in one or more of the outer tubes 1107.

Apparatus may be provided that facilitates bowing of one or more members of the outer tubes 1107 on an individual basis, rather than bowing in unison as has been described.

Different types of devices and apparatuses may be used for the tubes, to control and/or regulate their movement, and/or to feed them with radioactive seeds, then have been described. A radioactive source other than a seed may be used in addition or instead.

The patent applications that have been incorporated by reference in the Cross-Reference to Related Applications section of this application disclose a broad variety of related devices, components, and procedures. One or more of these may be used in conjunction with the devices, components, and/or procedures that are described in this application and/or in lieu of some or all of them.

Nothing that has been stated or illustrated is intended to cause a dedication of any component, step, feature, object, benefit, advantage, or equivalent to the public.

We claim:

1. A brachytherapy device comprising a plurality of rods, each configured to move between a straightened position and a bowed position, the plurality of rods configured to collectively form a shaft while each rod is in the straightened position and to collectively form at least one cage while at least some of the rods are in the bowed position, at least some of the rods having lumens that are configured to receive and hold radioactive material, wherein some of the rods are configured to form a first cylinder while in the straightened position and the other rods are configured to form a second cylinder while in the straightened position that surrounds the first cylinder, whereby the plurality of rods are further configured such that at least a substantial portion of each rod in the second cylinder lies between two rods within the first cylinder while in the straightened position.

2. The brachytherapy device of claim 1 further comprising a rotatable mechanism configured to move the second cylinder between the straightened position and the bowed position.

3. A brachytherapy device comprising a plurality of rods, each configured to move between a straightened position and a bowed position, the plurality of rods configured to collectively form a shaft while each rod is in the straightened position and to collectively form at least one cage while at least some of the rods are in the bowed position, at least some of the rods having lumens that are configured to receive and hold radioactive material, wherein each rod has opposing longitudinal flanges, each of which is configured to overlap with a longitudinal flange of a neighboring rod while in the straightened position.

4. The brachytherapy device of claim 3 further comprising a rotatable mechanism configured to move some of the rods between the straightened position and the bowed position.

5. A brachytherapy device comprising:
a first and a second set of rods, at least some of the rods having lumens that are configured to receive and hold radioactive material;
a group expansion mechanism associated with the first set of rods and configure to collectively move the first set of rods in unison, each between a straightened position and a bowed position, the first set of rods configured to collectively form a shaft while each of the first set of rods is in the straightened position and to collectively form a cage while each of the first set of rods is in the bowed position; and a rod bowing mechanism associated with each of the second set of rods and configured to individually move each of the second set of rods between a straightened and a bowed position, the second set of rods configured to collectively form a shaft while each of the second set of rods is in the straightened position.

6. The brachytherapy device of claim 5 wherein the group expansion mechanism includes a rotatable mechanism configured to move the first set of rods in unison between the straightened position and the bowed position.

7. A brachytherapy device comprising:

a plurality of rods configured to move between a straightened position and a bowed position, the rods configured to collectively form a shaft while each of the rods is in the straightened position, at least some of the rods having lumens configured to receive and hold radioactive material; and a plurality of actuators, each associate with one of the rods and configured to cause the rod with which it is associated to move from the straightened position to the bowed position in incremental steps, each of the incremental steps being delineated by a ratchet mechanism.

* * * * *